US00PP27428P2

(12) United States Plant Patent
Hurd

(10) Patent No.: US PP27,428 P2
(45) Date of Patent: Nov. 29, 2016

(54) ***VERONICA* PLANT NAMED 'VERY VAN GOGH'**

(50) Latin Name: ***Veronica* hybrid**
Varietal Denomination: Very Van Gogh

(71) Applicant: Kevin A. Hurd, Austin, TX (US)

(72) Inventor: Kevin A. Hurd, Austin, TX (US)

(73) Assignee: Walters Gardens, Inc, Zeeland, MI (US)

( * ) Notice: Subject to any disclaimer, the term of this patent is extended or adjusted under 35 U.S.C. 154(b) by 83 days.

(21) Appl. No.: 14/544,857

(22) Filed: Feb. 26, 2015

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt

(57) ABSTRACT

The new and distinct cultivar of hybrid ornamental spiked speedwell plant *Veronica* 'Very Van Gogh' with compact habit with upright habit and stiff, upright, heavily-branched spikes producing radiant rosy purple flowers over a long period and suitable as a potted plant, for the garden, and for cut flower arrangements.

1 Drawing Sheet

Botanical classification: *Veronica* hybrid.
Variety denomination: 'Very Van Gogh'.

BACKGROUND OF THE INVENTION

The present invention relates to the new and distinct cultivar of spiked speedwell, botanically known as *Veronica* hybrid, and hereinafter also referred to by the cultivar name 'Very Van Gogh' or "the new plant". The new plant selected as an individual seedling originally referenced as breeder code "K8-64-01B" was collected in the summer of 2008 by Kevin A. Hurd in the hybridizing greenhouses of a wholesale perennial nursery in Zeeland, Mich., USA, as an uncontrolled open pollination of *Veronica* hybrid 'Baby Doll' U.S. Plant Pat. No. 16,428. 'Baby Doll' is a hybrid cross of *Veronica longifolia*×*Veronica spicata*. The plant has been asexually propagated by basal shoot tip cuttings in the greenhouses at the same nursery in Zeeland, Mich., with subsequent asexually propagated plants found to be identical to the original selection with all the same traits as the original seedling.

BRIEF SUMMARY OF THE PLANT

*Veronica* 'Very Van Gogh' is unique from all other spiked speedwell known to the inventor. Several other cultivars have blue to purple flowers, but this is the only variety known by the applicant to have the following trait combinations.

Compared to the female parent, 'Baby Doll', the new plant is taller, with more branched scapes, and the flower color is less red and more purple pigmented.

The closest comparison varieties known to the inventor are *Veronica* 'Eveline' U.S. Plant Pat. No. 14,888 and *Veronica* 'Sweet Lullaby' U.S. Plant Pat. No. 23,611. The new plant has shorter, smaller foliage and more purple-pigmented flowers than both 'Eveline' and 'Sweet Lullaby' and is much taller with more branched scapes than 'Sweet Lullaby'. 'Very Van Gogh' is taller than 'Giles van Hees' (not patented) and less red and more purple pigmented in flower. The new plant is more rosy purple than 'Hocus Pocus' U.S. Plant Pat. No. 23,853 and 'Red Fox' (not patented).

Table 1 below shows a more concise comparison of some of the other nearest spike speedwell cultivars:

TABLE 1

VERONICA Comparisons

| CULTIVAR | Plant Height | Flower Color |
|---|---|---|
| 'Baby Doll' | 38 cm | light red purple |
| 'Eveline' | 50 cm | purplish red |
| 'Giles van Hees' | 20 cm | bright pink |
| 'Hocus Pocus' | 50 cm | violet purple |
| 'Red Fox' | 38 cm | fuchsia pink |
| 'Sweet Lullaby' | 20 cm | baby pink |
| 'Very Van Gogh' | 46 cm | rosy purple |

The following are traits of *Veronica* 'Very Van Gogh' that in combination distinguish it from all other spiked speedwell known to the inventor:

1. Tall, well-branched scapes producing continuous heavy flower show.
2. Numerous self-cleaning flowers of distinctly radiant rosy purple petals in mid-summer.
3. Ovate foliage of bright green.

BRIEF DESCRIPTION OF THE DRAWINGS

The photograph of the new plant demonstrates the overall appearance and unique traits of 'Very Van Gogh' as a two-year old plant grown in a full-sun trial garden in Zeeland, Mich. with supplemental water and fertilizer provided as needed. The colors are as accurate as reasonably possible with color reproductions. Variation in ambient light spectrum, source and direction may cause the appearance of minor variation in color.

DETAILED BOTANICAL DESCRIPTION

Figure 1:
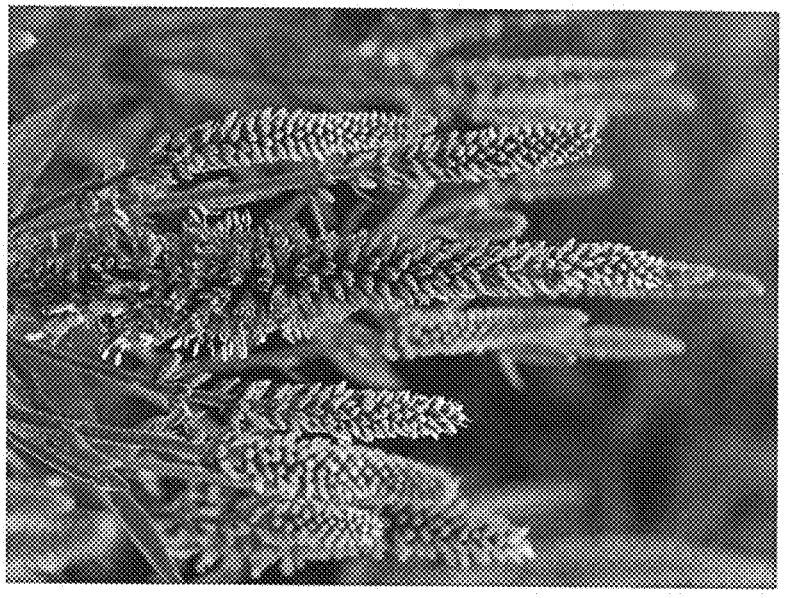
FIG. 1 shows a close-up of the scape and flowers.
Figure 2:
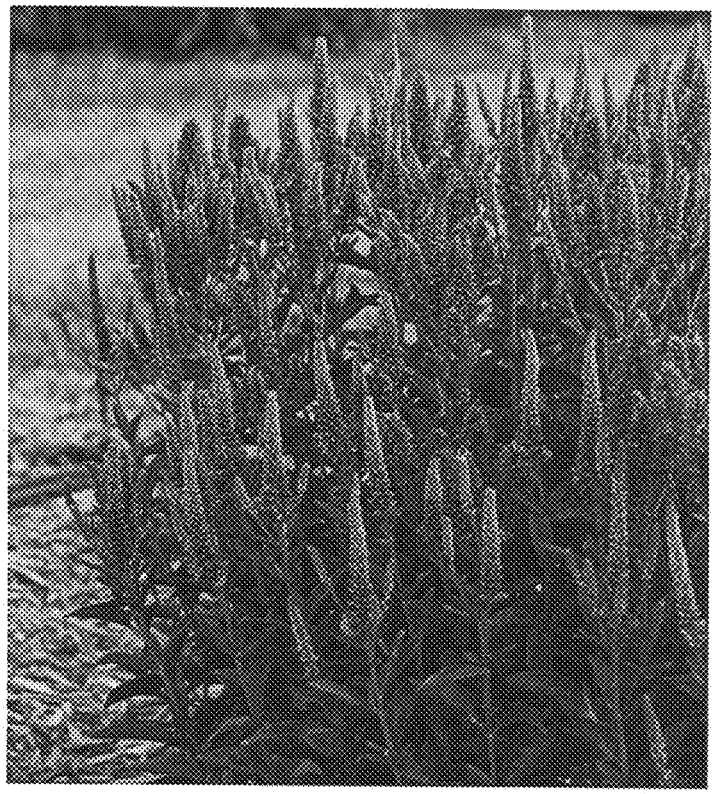
FIG. 2 shows the plant in the landscape in mid-summer.

The following descriptions and color references of a greenhouse-grown one-year old plant of 'Very Van Gogh' are based on the 2001 edition of The Royal Horticultural Society Colour Chart except where common dictionary terms are used. *Veronica* 'Very Van Gogh' has not been observed under all possible environments. The phenotype may vary slightly with different growing environments such as temperature, light, fertility, soil pH, moisture and maturity levels, but without any change in the genotype. The following observations and size descriptions are based on two-year old plants in the full-sun trial garden of a nursery in Zeeland, Mich. with supplemental fertilizer and water as needed.

Botanical classification: *Veronica* hybrid.

Parentage: Female (seed parent) *Veronica* 'Baby Doll' U.S. Plant Pat. No. 16,428; male (pollen parent) unknown.

Plant habit: Hardy herbaceous perennial, compact, with several stems, average about 46.0 cm tall in flower and about 58 cm wide; flowering beginning early July in Michigan and continuing for about 5 weeks with occasional repeat if deadheaded.

Leaves: Simple, flat, elliptic to ovate, opposite, serrulate, minutely pubescent below and above; acute apex, cuneate to rounded base; average about 6.5 cm long by about 2.5 cm wide decreasing in both length, and width distally.

*Leaf color*.—Adaxial nearest RHS 137B; abaxial between RHS 138A and RHS 138B.

Veins: Reticulate, minutely pubescent below and above; main vein about 1.0 mm diameter at abaxial base and about 0.5 mm at adaxial base.

*Vein color*.—Adaxial proximal half of center vein and proximal secondary veins within about 7 mm of main vein between RHS 145C and RHS 145D with slight tinting of nearest RHS 186D on main vein, gradually darkening within distal one-half and toward margin to nearest RHS 137B; abaxial proximal one-half of center vein and secondary veins nearest to center vein on abaxial surface nearest RHS 145C, gradually darkening to between RHS 138A and RHS 138B in the distal one-half and toward margin.

Petiole: Simple, concaved upward on adaxial side, rounded on abaxial side; minutely pubescent above and below; about 0.5 to about 1.0 cm long and about 1.5 mm wide, distally shorter; average about 0.7 mm long and about 1.5 mm wide.

*Petiole color*.—Adaxial side nearest RHS 137B near margin, center between RHS 145C and RHS 145D, with slight tinting of nearest RHS 186D; abaxial side between RHS 138A and RHS 138B on margins and nearest RHS 145C in center.

Buds two days prior to opening: Convolute, narrowly oblong, obtuse apex; about 6.0 mm long and 2.5 mm diameter.

*Bud color*.—Nearest RHS N74C one to two days prior to opening; buds seven to eight days prior to opening nearest RHS 73B in distal half, lightning lightening to lighter than RHS 73D in the basal one-half inside of calyx.

Flowers: Simple, campanulate; on heavily branched upright to spikes; numerous, congested, approximately 200 per main spike and about 150 flowers per secondary branch; about 4.5 mm across, about 5.0 mm tall and about 6.0 mm deep; no detectible fragrance; flowers persist individually for 4 to 6 days whether on the plant or as cut flower; self-cleaning.

Petals: Four; margin entire; one larger petal above and three slightly small below, with rounded apex and fused in basal one-half; larger petal about 9.0 mm long by about 2.5 mm wide, smaller petals about 8.5 mm long and about 1.5 mm wide; glabrous outer and inner surfaces.

*Petal color*.—When initially opening adaxial and abaxial surfaces apex nearest RHS N78B; after two days opened adaxial and abaxial surfaces nearest RHS 77B; base of petals in calyx lighter than between RHS 75D and RHS 76D.

Androecium: Stamens two, exserted.

*Filaments*.—Two, fused to lower portion of petal; about 7.0 mm by 0.3 mm; color between RHS 76B and RHS 76C.

*Anther*.—Oblong to elliptic; dorsifixed, longitudinal, with anther sides bent back around filament in about a 270 degree angle; each half with acute apex; about 2.3 mm by about 1.0 mm.

*Anther color*.—Variable; younger anthers nearest RHS N77B; older anthers between RHS N186B and RHS N77A.

*Pollen*.—Abundant, globose, less than 0.1 mm; nearest RHS 158C.

Gynoecium: Single; simple.

*Style*.—Single; straight, extending perpendicular to flower face; about 7.5 mm long by about 0.25 mm diameter; color between RHS 77A and RHS 77B; darker distally and lighter at base; persists after petals drop.

*Stigma*.—Semi-spherical; about 0.5 mm in diameter; color between RHS 76D and RHS 84D.

*Ovary*.—Spherical; about 1.0 mm in diameter; nearest RHS 144A.

Sepals: Four; entire, surface dull, ovate to narrowly ovate, acute apex, base fused forming corolla, sparsely pubescent with minute glandular hairs, upper pair about 3.0 mm long and about 0.5 mm wide, lower pair about 4.0 mm long by about 0.5 mm wide, nearest RHS 137A both surfaces with light tinting of nearest RHS N186C in regions getting intense direct sunlight.

Peduncle: About 28 per plant; heavily-branched raceme, strong, erect, rounded cross section, minutely pubescent; about 46.0 cm long and about 3.0 mm in diameter at the base, flowering section of the primary stem about 14.0 long; diameter of flowering portion of raceme about 2.5 cm; freely branching at nearly every node; about 8 to 9 nodes; internode length about 3.7 cm.

*Peduncle color*.—Between RHS 138A and RHS 138B with frequent tinted regions between RHS 182B and RHS 184B, especially where exposed to more direct sun.

Pedicel: Upright, rigid, rounded in cross section; about 1.0 mm long and 0.5 mm diameter, sparsely pubescent with minute hairs.

*Pedicel color*.—Nearest RHS 137A.

Bract: Single subtending each flower, linear, narrowly acute apex, entire, sessile, based fused to peduncle, proximal bracts about 1.2 cm long and about 2.0 mm wide and decreasing distally to about 3.0 mm long and less than about 0.5 mm wide.

*Bract color*.—RHS 137A above and RHS 137C below.

Fruit: Emarginate, globose, loculicidal capsule; about 3.0 mm diameter.

Seed: Elliptic, about 1.0 mm long; between RHS 166A and RHS 166B.

Propagation: Stem and tip cuttings root in about 2 weeks and finish to flowering in a 3.8 liter container in 8 to 10 weeks following a vernalization period of about 8 weeks.

Hardiness, pest and disease resistance: The plant grows best with adequate moisture and drainage, but is able to tolerate some drought when mature. Hardiness at least from USDA zone 4 through 8. Disease and pest resistance beyond what is typical of that common to other spiked speedwell has not been observed.

I claim:

1. A new and distinct cultivar of ornamental spiked speedwell plant, *Veronica* 'Very Van Gogh', as herein described and illustrated, with upright habit and stiff, upright, heavily-branched spikes producing radiant rosy purple flowers over a long period and suitable as a potted plant, for the garden, and for cut flower arrangements.

* * * * *